United States Patent
Tonomura et al.

(10) Patent No.: US 7,202,375 B2
(45) Date of Patent: Apr. 10, 2007

(54) BISSILYLAMINO GROUP-BEARING CHLOROSILANE COMPOUND AND PREPARATION METHOD, AND METHOD OF PREPARING BISSILYLAMINO GROUP-BEARING ORGANOOXYSILANE COMPOUND

(75) Inventors: Yoichi Tonomura, Niigata-ken (JP); Tohru Kubota, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 378 days.

(21) Appl. No.: 10/854,180

(22) Filed: May 27, 2004

(65) Prior Publication Data

US 2004/0242911 A1    Dec. 2, 2004

(30) Foreign Application Priority Data

May 30, 2003   (JP)   ............................. 2003-155368

(51) Int. Cl.
 *C07F 7/10*    (2006.01)
(52) U.S. Cl. ..................................... 556/425
(58) Field of Classification Search ................ 556/425
See application file for complete search history.

(56) References Cited

U.S. PATENT DOCUMENTS 2,762,823 A * 9/1956 Speier, Jr. ................... 556/425

FOREIGN PATENT DOCUMENTS

JP          10-17579 A       1/1998

OTHER PUBLICATIONS

Boutevin et al., *Makromol. Chem.*, 190:2437-2447 (1989).

* cited by examiner

*Primary Examiner*—Samuel Barts
(74) *Attorney, Agent, or Firm*—Birch, Stewart, Kolasch & Birch, LLP

(57) ABSTRACT

Bissilylamino group-bearing chlorosilane compounds of formula (1):

$$[(CH_3)_3Si]_2NCH_2CH_2CH_2Si(CH_3)_nCl_{3-n} \qquad (1)$$

wherein n is 0 or 1 are novel. They are useful as silane coupling agents and surface treating agents. They can be readily converted, through reaction with alcohols, to bissilyl group-bearing alkoxysilane compounds which are useful as intermediates for the synthesis of aminopropyl-modified silicone oil. The invention also provides an industrially advantageous method capable of preparing the bissilylamino group-bearing chlorosilane compounds.

3 Claims, 2 Drawing Sheets

BISSILYLAMINO GROUP-BEARING CHLOROSILANE COMPOUND AND PREPARATION METHOD, AND METHOD OF PREPARING BISSILYLAMINO GROUP-BEARING ORGANOOXYSILANE COMPOUND

This Nonprovisional application claims priority under 35 U.S.C. §119(a) on patent application No(s). 2003-155368 filed in JAPAN on May 30, 2003, the entire contents of which are hereby incorporated by reference.

TECHNICAL FIELD

This invention relates to novel bissilylamino group-bearing chlorosilane compounds which are useful as silane coupling agents, surface treating agents and reactants to aminopropyl-modified silicone oil, a method for preparing the same, and a method for preparing bissilylamino group-bearing organooxysilane compounds.

BACKGROUND ART

Aminopropylalkoxysilanes such as aminopropyltrialkoxy-silanes and aminopropylmethyldialkoxysilanes and bissilylamino group-bearing alkoxysilane compounds described in JP-A 10-17579 are widely used as silane coupling agents and surface treating agents.

These aminopropylalkoxysilanes and bissilylamino group-bearing alkoxysilane compounds attain the intended purpose by the mechanism that alcohol-removing condensation reaction occurs between alkoxysilyl groups on the compounds and hydroxyl groups on the surface of silica or substrates to introduce aminopropyl groups. However, since the reaction of alkoxysilyl groups with hydroxyl groups is slow, it is difficult to silylate hydroxyl groups in a quantitative manner.

One means of solving this problem is the use of chlorosilane compounds. However, chlorosilane compounds having a primary amino group do not exist because the amino group reacts with a silicon-chlorine moiety. Therefore, the use of chlorosilane compounds fails to achieve satisfactory introduction of the desired aminopropyl group.

It would be desirable to have silane compounds which overcome the above-mentioned problem, facilitate the introduction of a desired aminopropyl group, and are useful as silane coupling agents, surface treating agents and reactants for use in the synthesis of aminopropyl-modified silicone oil.

SUMMARY OF THE INVENTION

An object of the invention is to provide novel chlorosilane compounds which ensure easy and effective introduction of a desired aminopropyl group, and a method for preparing the same. Another object is to provide a method for preparing bissilylamino group-bearing organooxysilane compounds.

The inventor has found that a bissilylamino group-bearing chlorosilane compound of the general formula (1):

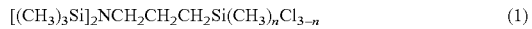

wherein n is 0 or 1 is obtained by reacting N,N-bistrimethylsilylallylamine with a hydrogenchlorosilane compound of the general formula (2):

wherein n is 0 or 1 in the presence of a platinum catalyst, and is useful as a chlorosilane compound capable of introducing a desired aminopropyl group.

It has also been found that by reacting a bissilylamino group-bearing chlorosilane compound of the general formula (1'):

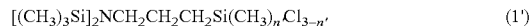

wherein n' is 0, 1 or 2, with a compound of the general formula (3):

$$ROH \qquad (3)$$

wherein R is a hydrocarbon group of 1 to 10 carbon atoms for organooxy-conversion, a bissilylamino group-bearing organooxysilane compound of the general formula (4):

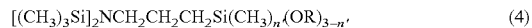

wherein R is a hydrocarbon group of 1 to 10 carbon atoms and n' is 0, 1 or 2, can be easily produced in high yields.

More particularly, a compound of formula (1), in which the hydrogen atoms on the amino group are substituted with trimethylsilyl groups, can exist stable in a chlorosilane form. When silica or a substrate is treated with this compound, quantitative reaction with hydroxyl groups on the surface of silica or substrate can take place. When the reaction is followed by hydrolysis of bonds of trimethylsilyl groups with nitrogen, amino groups are regenerated so that the desired aminopropyl groups are introduced into the silica or substrate. The purposes of silane coupling agents and surface treating agents are achieved in this way.

By reacting a bissilylamino group-bearing chlorosilane compound of formula (1') with an alcohol of formula (3), it can be readily converted into a bissilylamino group-bearing organooxysilane compound of formula (4) which is useful as an intermediate reactant for the synthesis of aminopropyl-modified silicone oil described in JP-A 10-17579, silane coupling agent or surface treating agent. The present invention is predicated on these findings.

As compared with the method of JP-A 10-17579 by the same assignee as the present invention, the method for preparing a bissilylamino group-bearing organooxysilane compound according to the second embodiment of the invention has industrial advantages that preparation is possible without a need for hydrogenalkoxysilanes which are unstable and awkward to handle, and a variety of alkoxysilanes can be produced.

Therefore, the present invention provides:

(i) a bissilylamino group-bearing chlorosilane compound of formula (1);

(ii) a method for preparing a bissilylamino group-bearing chlorosilane compound of formula (1), comprising the step of reacting N,N-bistrimethylsilylallylamine with a hydrogenchlorosilane compound of formula (2) in the presence of a platinum catalyst; and (iii) a method for preparing a bissilylamino group-bearing organooxysilane compound of formula (4), comprising the step of reacting a bissilylamino group-bearing chlorosilane compound of formula (1') with a compound of formula (3) for converting the chlorosilane compound into the corresponding organooxysilane compound.

DESCRIPTION OF THE PREFERRED EMBODIMENTS

Figure 1:
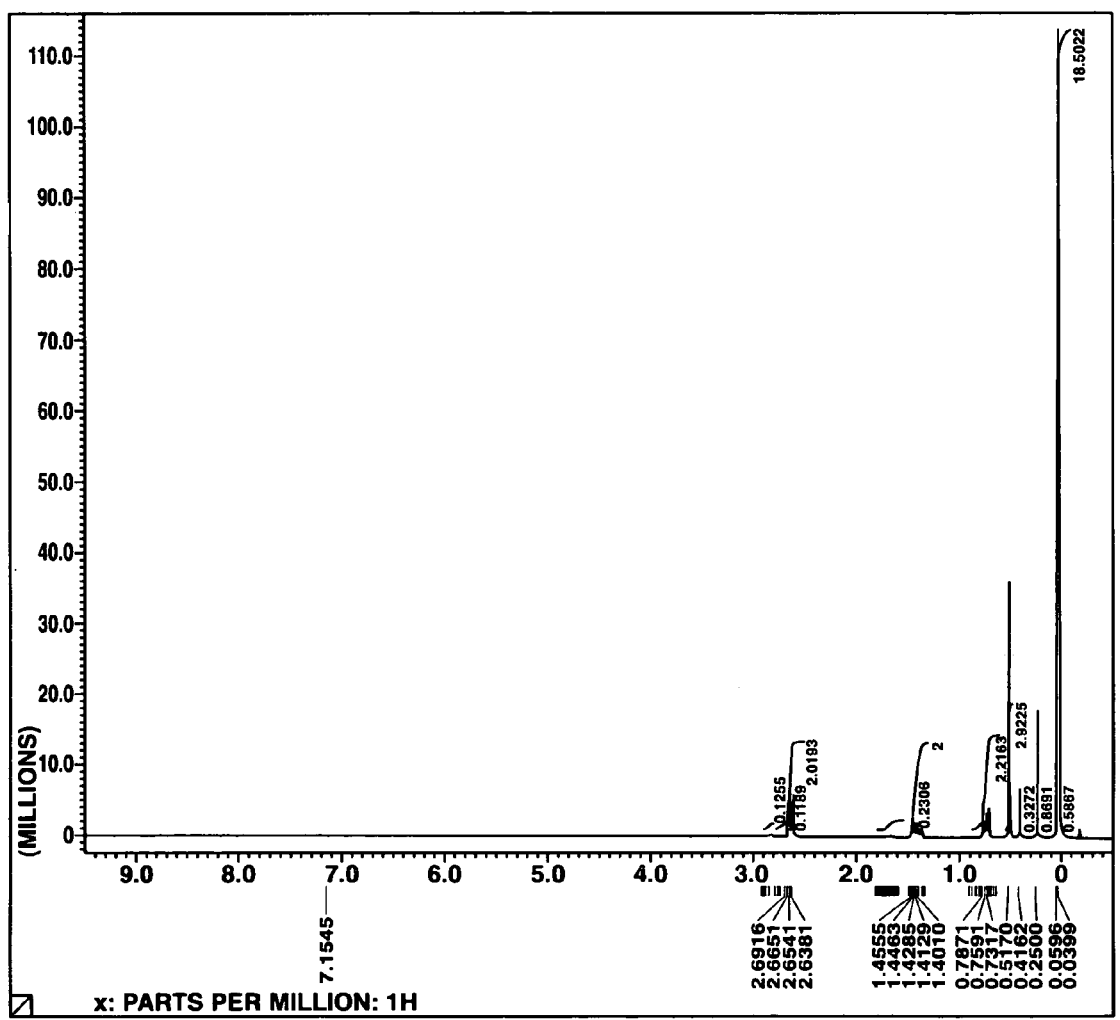
FIG. 1 is a diagram of nuclear magnetic resonance spectrum of the compound obtained in Example 1.

The first embodiment of the invention is a bissilylamino group-bearing chlorosilane compound of the general formula (1):

$$[(CH_3)_3Si]_2NCH_2CH_2CH_2Si(CH_3)_nCl_{3-n} \quad (1)$$

wherein n is 0 or 1. Specifically the bissilylamino group-bearing chlorosilane compounds of formula (1) are N,N-bis(trimethylsilyl)aminopropylmethyldichlorosilane and N,N-bis(trimethylsilyl)aminopropyltrichlorosilane.

The method for preparing a bissilylamino group-bearing chlorosilane compound of formula (1) is, for example, by reacting N,N-bistrimethylsilylallylamine with a hydrogenchlorosilane compound of the general formula (2):

$$HSi(CH_3)_nCl_{3-n} \quad (2)$$

wherein n is 0 or 1, in the presence of a platinum catalyst.

Specifically, the hydrogenchlorosilane compounds of formula (2) are methyldichlorosilane and trichlorosilane.

For this reaction, N,N-bistrimethylsilylallylamine and the hydrogenchlorosilane compound of formula (2) may be used in any desired proportion. From the reactivity and productivity standpoints, 0.5 to 2 moles, especially 0.8 to 1.2 moles of the hydrogenchlorosilane compound is preferably used per mole of N,N-bistrimethylsilylallylamine.

The platinum catalyst used in the reaction is a catalyst containing a platinum group metal. Examples include chloroplatinic acid, alcohol solutions of chloroplatinic acid, toluene or xylene solutions of platinum-1,3-divinyl-1,1,3,3-tetramethyldisiloxane complex, tetrakis (triphenylphosphine) platinum, dichlorobis (triphenylphosphine) platinum, dichlorobis (acetonitrile) platinum, dichlorobis (benzonitrile) platinum, and dichlorocyclooctadieneplatinum.

The platinum catalyst may be used in any desired amount. From the reactivity and productivity standpoints, the platinum catalyst is preferably used in an amount of 0.000001 to 0.01 mole, especially 0.00001 to 0.001 mole, calculated as platinum metal, per mole of N,N-bistrimethylsilylallylamine.

The temperature at which the reaction is carried out is not particularly limited although a temperature of 0 to 120° C., especially 20 to 100° C. is preferred. The reaction time is preferably about 1 to 20 hours.

A solvent may be used although the reaction can proceed without a solvent. Suitable solvents include hydrocarbon solvents such as pentane, hexane, cyclohexane, heptane, isooctane, benzene, toluene and xylene; ether solvents such as diethyl ether, tetrahydrofuran and dioxane; ester solvents such as ethyl acetate and butyl acetate; aprotic polar solvents such as acetonitrile and N,N-dimethylformamide; and chlorinated hydrocarbon solvents such as dichloromethane and chloroform. The solvents may be used alone or in admixture of any and in conventional amounts.

The bissilylamino group-bearing chlorosilane compound of formula (1), in which hydrogen atoms on the amino group are substituted with trimethylsilyl groups, is free from the preferential reaction of an amino group with a silicon-chlorine moiety and can exist as a stable chlorosilane. When silica or a substrate is treated with this compound, quantitative reaction with hydroxyl groups on the surface of silica or substrate can take place. When the reaction is followed by hydrolysis of bonds of trimethylsilyl groups with nitrogen, amino groups are regenerated so that the desired aminopropyl groups are introduced into the surface of silica or substrate.

The chlorosilane compound of formula (1) is useful in itself. When a bissilylamino group-bearing chlorosilane compound of the general formula (1'):

$$[(CH_3)_3Si]_2NCH_2CH_2CH_2Si(CH_3)_{n'}Cl_{3-n'} \quad (1')$$

wherein n' is 0, 1 or 2, is reacted with a compound of the general formula (3), there is obtained a bissilylamino group-bearing organooxysilane compound of the general formula (4):

$$[(CH_3)_3Si]_2NCH_2CH_2CH_2Si(CH_3)_{n'}(OR)_{3-n'} \quad (4)$$

wherein R is a hydrocarbon group of 1 to 10 carbon atoms and n' is 0, 1 or 2. The organooxysilane compound of formula (4) is useful as an intermediate reactant for the synthesis of aminopropyl-modified silicone oil or the like.

One reactant used in producing the bissilylamino group-bearing organooxysilane compound of formula (4) is a compound of the general formula (3):

$$ROH \quad (3)$$

wherein R is a hydrocarbon group of 1 to 10 carbon atoms.

Illustrative, non-limiting examples of the compound of formula (3) include alcohols such as methanol, ethanol, 1-propanol, 2-propanol, 1-butanol, 2-butanol, 2-methyl-1-propanol, 2-methyl-2-propanol, 1-pentanol, 2-pentanol, 2-methyl-2-butanol, 4-methyl-2-pentanol, and 2-ethyl-1-hexanol, as well as phenols, benzyl alcohol and allyl alcohol. Inter alia, methanol and ethanol are preferred.

An appropriate amount of the compound of formula (3) used is 0.5 to 2.0 moles, especially 0.8 to 1.2 moles, per mole of Si—Cl bonds in the compound of formula (1').

Since hydrogen chloride is formed in the organoxy-forming reaction, a basic compound may be present in the reaction system for capturing or scavenging the hydrogen chloride. Examples of suitable basic compounds include amines such as methylamine, dimethylamine, trimethylamine, ethylamine, diethylamine, triethylamine, methyldiisopropylamine, butylamine, dibutylamine, tributylamine, 2-ethylhexylamine, ethylenediamine, pyrrolidine, N-methylpyrrolidine, piperidine, N-methylpiperidine, aniline, N-methylaniline, N,N-dimethylaniline, and toluidine; nitrogen-containing aromatic compounds such as pyridine, quinoline, isoquinoline, picoline and lutidine; ammonia; and metal alkoxides such as sodium methoxide and sodium ethoxide.

An appropriate amount of the basic compound used is 0.5 to 2.0 moles, especially 0.8 to 1.2 moles, per mole of Si—Cl bonds in the compound of formula (1').

A solvent may be used although the above reaction can proceed without a solvent. Suitable solvents include hydrocarbon solvents such as pentane, hexane, cyclohexane, heptane, isooctane, benzene, toluene and xylene; ether solvents such as diethyl ether, tetrahydrofuran and dioxane; ester solvents such as ethyl acetate and butyl acetate; aprotic polar solvents such as acetonitrile and N,N-dimethylformamide; and chlorinated hydrocarbon solvents such as dichloromethane and chloroform. The solvents may be used alone or in admixture of any and in conventional amounts.

The reaction conditions are not critical although a temperature of −20° C. to 150° C., especially 0° C. to 100° C. and a time of about 1 to 20 hours, especially about 2 to 10 hours are preferred.

EXAMPLE

Examples of the invention are given below by way of illustration and not by way of limitation.

Example 1

A flask equipped with a stirrer, reflux condenser, dropping funnel and thermometer was charged with 60.5 g (0.3 mol) of N,N-bis(trimethylsilyl)allylamine and 0.20 g of a toluene solution of platinum-1,3-divinyl-1,1,3,3-tetramethyl-disiloxane complex (platinum content 3 wt %). At an internal temperature of 60 to 70° C., 36.2 g (0.315 mol) of methyldichlorosilane was added dropwise over 2 hours. Then the contents were stirred for one hour at the temperature. The reaction solution was distilled, collecting 81.8 g of a fraction having a boiling point of 73–74° C./40 Pa.

The fraction was analyzed by mass spectrometry, nuclear magnetic resonance spectroscopy ($^1$H-NMR) and infrared absorption spectroscopy (IR), with the results shown below.

Figure 2:
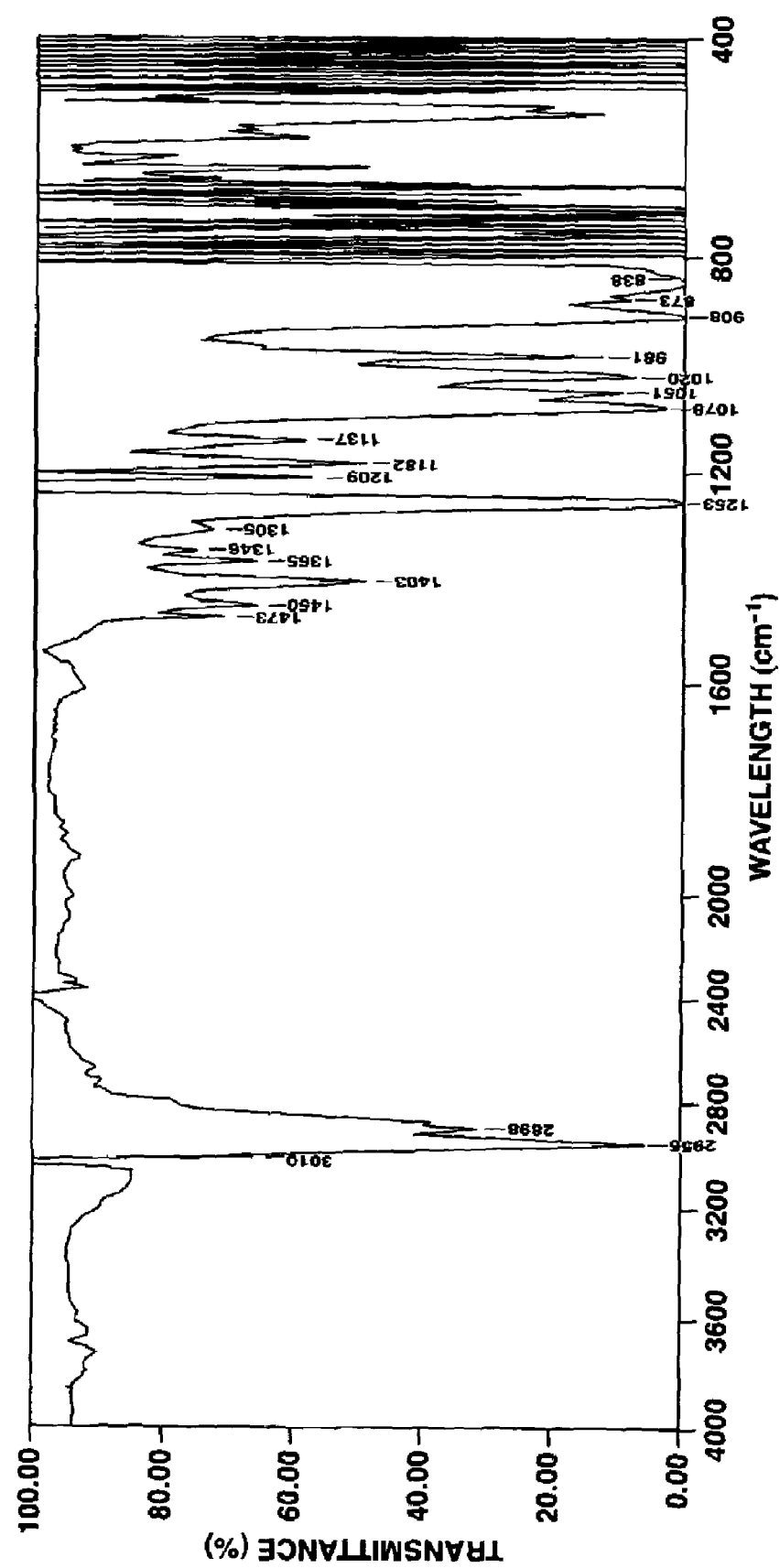
FIG. 2 is a diagram of infrared absorption spectrum of the compound obtained in Example 1.

Mass spectrum: m/z 315, 192, 174, 73, 59 $^1$H-NMR (heavy benzene solvent): FIG. 1 IR: FIG. 2

Based on these data, the compound was identified to be N,N-bis (trimethylsilyl) aminopropylmethyldichlorosilane.

Example 2

A reactor was charged with 63.3 g (0.20 mol) of N,N-bis (trimethylsilyl) aminopropylmethyldichlorosilane obtained in Example 1, 22.3 g (0.44 mol) of triethylamine and 120 ml of toluene. To the reactor at 20 to 300° C., 14.1 g (0.44 mol) of methanol was added dropwise over 2 hours, followed by one hour of stirring at the temperature. Thereafter, 60 g of water was added to the reaction solution. The triethylamine hydrogen chloride formed was dissolved and separated off. The organic layer was distilled, collecting 58.0 g of a fraction having a boiling point of 115–120° C./0.67 kPa. On analysis by mass spectrometry, $^1$H-NMR and IR spectroscopy, the fraction was identified to be bis (trimethylsilyl) aminopropylmethyldimethoxysilane (yield 94%).

Example 3

A reactor was charged with 63.3 g (0.20 mol) of N,N-bis (trimethylsilyl) aminopropylmethyldichlorosilane obtained in Example 1, 22.3 g (0.44 mol) of triethylamine and 120 ml of toluene. To the reactor at 20 to 30° C., 20.3 g (0.44 mol) of ethanol was added dropwise over 2 hours, followed by one hour of stirring at the temperature. Thereafter, 60 g of water was added to the reaction solution. The triethylamine hydrogen chloride formed was dissolved and separated off. The organic layer was distilled, collecting 63.9 g of a fraction having a boiling point of 94–95° C./0.13 kPa. On analysis by mass spectrometry, $^1$H-NMR and IR spectroscopy, the fraction was identified to be bis (trimethylsilyl) aminopropylmethyldiethoxysilane (yield 95%).

Example 4

A flask equipped with a stirrer, reflux condenser, dropping funnel and thermometer was charged with 592.2 g (2.0 mol) of N,N-bis(trimethylsilyl)aminopropyldimethylchloro-silane, 222.6 g (2.2 mol) of triethylamine and 800 ml of toluene. To the flask at 20 to 30° C., 70.4 g (2.2 mol) of methanol was added dropwise over 2 hours, followed by one hour of stirring at the temperature. Thereafter, 300 g of water was added to the reaction solution. The triethylamine hydrogen chloride formed was dissolved and separated off. The organic layer was distilled, collecting 537.8 g of a fraction having a boiling point of 90° C./0.4 kPa. On analysis by mass spectrometry, $^1$H-NMR and IR spectroscopy, the fraction was identified to be bis(trimethylsilyl)aminopropyldimethylmethoxysilane (yield 92%).

Example 5

A flask equipped with a stirrer, reflux condenser, dropping funnel and thermometer was charged with 148.1 g (0.5 mol) of N,N-bis(trimethylsilyl)aminopropyldimethylchloro-silane, 55.7 g (0.55 mol) of triethylamine and 200 ml of toluene. To the flask at 20 to 30° C., 25.4 g (0.55 mol) of ethanol was added dropwise over 2 hours, followed by one hour of stirring at the temperature. Thereafter, 75 g of water was added to the reaction solution. The triethylamine hydrogen chloride formed was dissolved and separated off. The organic layer was distilled, collecting 134.5 g of a fraction having a boiling point of 98–102° C./0.4 kPa. On analysis by mass spectrometry, $^1$H-NMR and IR spectroscopy, the fraction was identified to be bis(trimethylsilyl)amino-propyldimethylethoxysilane (yield 88%).

The novel bissilylamino group-bearing chlorosilane compounds of the invention are useful not only as silane coupling agents, surface treating agents and the like, but also as synthesis intermediates. Namely, by reacting with compounds of formula (3), they can be readily converted, in high yields, to bissilylamino group-bearing organooxysilane compounds which are useful as intermediates for the synthesis of aminopropyl-modified silicone oil or the like. The method of the invention is capable of preparing bissilylamino group-bearing chlorosilane compounds in an industrially advantageous manner.

Japanese Patent Application No. 2003-155368 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A bissilylamino group-bearing chlorosilane compound of the general formula (1):

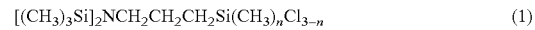

wherein n is 0.

2. A method for preparing a bissilylamino group-bearing chlorosilane compound of the general formula (1):

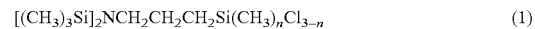

wherein n is 0 or 1
comprising the step of reacting N,N-bistrimethylsilylallylamine with a hydrogenchlorosilane compound of the general formula (2):

wherein n is 0 or 1, in the presence of a platinum catalyst.

3. A method for preparing a bissilylamino group-bearing organooxysilane compound of the general formula (4):

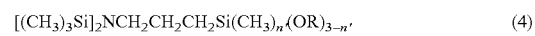

wherein R is a hydrocarbon group of 1 to 10 carbon atoms and n' is 0, 1 or 2, said method comprising the step of reacting a bissilylamino group-bearing chlorosilane compound of the general formula (1'):

(1')     $[(CH_3)_3Si]_2NCH_2CH_2CH_2Si(CH_3)_nCl_{3-n'}$ wherein n' is 0, 1 or 2, with a compound of the general formula (3):

ROH     (3)

wherein R is a hydrocarbon group of 1 to 10 carbon atoms for forming the organooxysilane compound.

* * * * *